United States Patent [19]

Charlet et al.

[11] 4,327,078
[45] Apr. 27, 1982

[54] COSMETIC AGENTS INCLUDING SOLUBLE ELASTIN

[75] Inventors: Egbert Charlet, Rösrath; Martin Kludas, Berlin, both of Fed. Rep. of Germany

[73] Assignee: Bayer Aktiengesellschaft, Leverkusen, Fed. Rep. of Germany

[21] Appl. No.: 17,773

[22] Filed: Mar. 5, 1979

Related U.S. Application Data

[63] Continuation of Ser. No. 856,562, Dec. 1, 1977, abandoned.

[30] Foreign Application Priority Data

Dec. 11, 1976 [DE] Fed. Rep. of Germany ....... 2656226
Oct. 7, 1977 [DE] Fed. Rep. of Germany ....... 2745284

[51] Int. Cl.³ .......................... A61K 7/00; A61K 7/42; A61K 7/48
[52] U.S. Cl. ........................................ 424/45; 424/47; 424/59; 424/70; 424/95; 424/177; 424/359
[58] Field of Search ....................... 424/45, 47, 70, 59, 424/95, 177, 359

[56] References Cited

U.S. PATENT DOCUMENTS 3,855,196 12/1974 Matsukawa ......................... 424/359
4,179,333 12/1979 Braeumer ............................ 424/359
4,186,188 1/1980 Gumprecht ......................... 424/359

FOREIGN PATENT DOCUMENTS 2804024 8/1979 Fed. Rep. of Germany ...... 424/359

OTHER PUBLICATIONS

Castellani, Chem. Abs., vol. 66, 1967, Ab No. 101891j.
Robert, Chem. Abs., vol. 75, 1971, Ab No. 107642m.
Deasy, Chem. Abs., vol. 76, 1972, Ab No. 82468q.
Sabetay, Chem. Abs., vol. 76, 1972, Ab. No. 131392w.
Fischer, Chem. Abs., vol. 84, 1976, Ab No. 27774b.

Primary Examiner—Anna P. Fagelson
Attorney, Agent, or Firm—Sprung, Felfe, Horn, Lynch & Kramer

[57] ABSTRACT

The invention concerns the provision of cosmetic agents containing, as an active ingredient, soluble elastin. Also included is a method of combating skin ageing by applying said cosmetic agents to the skin.

7 Claims, No Drawings

COSMETIC AGENTS INCLUDING SOLUBLE ELASTIN

This is a continuation of application Ser. No. 856,562, filed Dec. 1, 1977, abandoned.

The present invention relates to the use of soluble elastin as a constituent of cosmetic agents.

Elastin is the main protein substance present in elastic fibres and occurs in tendons, blood vessels and connective tissue. It is obtainable in the form of a brittle, fibrous, yellowish material which is insoluble in water, alcohol and ether and soluble in concentrated aqueous alkali metal hydroxide solutions. Its extreme insolubility and rubber-like properties, together with its high swellability, suggest that the proteins of elastin consist of long, unoriented, coiled polypeptide chains which are firmly linked with one another chemically at certain intervals by shorter side chains (F. Hermann, H. Ippen, H. Schaefer and G. Stüttgen Biochemie der Haut (Biochemistry of Skin), Georg Thieme Verlag Stuttgart, 1973, page 117-118).

On mild hydrolysis of elastin from the neck tendons of young calves, which have first been cleaned, defatted and comminuted, with boiling, aqueous dilute oxalic acid, hydrolysed elastin fractions which are water-soluble are formed, evidently by disintegration of the three-dimensional network [Römpps Chemie-Lexikon, (Römpp's Chemical Dictionary), Frankckh'sche Verlagshandlung, Stuttgart, 7th edition, 1973, page 970-971; Partidg S. M., Davis H. F. and Adair G. S., Biochem. J. 61 (1955), page 11-21; and Kellér S. and Mandl J., Biochem. Medicine 5, (1971), page 342-347].

These fractions hereinafter referred to as "soluble elastin", are dialysed against demineralised water, in order to remove low-molecular weight constituents, in particular amino acids and oxalic acid, and filtered. A clear, colourless, aqueous soluble elastin solution is thereby obtained in which usually about 80% of the soluble elastin has a molecular weight in the range of from 3,000 to 10,000, of the order of 10% of the soluble elastin has a molecular weight in the range of from 10,000 to 25,000 and less than 20%, preferably about 10% of the soluble elastin has a molecular weight in the range of from 25,000 to 100,000. This soluble elastin retains its native structure, which can be demonstrated by the activity of the elastin-specific enzyme "elastase".

Soluble elastin has not previously been used as a constituent of cosmetic agents.

It has now been found that soluble elastin is outstandingly suitable as a constituent of cosmetic agents.

By supplying soluble elastin, it is possible, to delay the withering of young elastin and the qualitative changes in the elastin in ageing skin, or to improve the quality of the skin. In addition, loss of elastin can be compensated for and a visible cosmetic effect can be achieved.

The physiological ageing process of skin plays a very decisive part in cosmetics. Whilst it cannot be halted, it is desirable that it should be retarded. This is particularly so in the case of facial skin, which is exposed to light and on which the visible ageing processes take place to a particularly large extent. Surprisingly, it has now been found that skin care agents containing soluble elastin have valuable prophylactic.

The aqueous solution of elastin prepared as described above is normally at from 0.2 to 0.5% strength solution which may be employed directly as a constituent of cosmetic agents, such as emulsions, lotions, sprays, ointments, creams and foam masks.

The finished products conveniently contain up to 10% by weight but preferably 2 to 5% of such a solution though of course more concentrated or more dilute solutions may also be used in greater or lesser amounts.

The soluble elastin-containing agents according to the invention may be employed for external application and may be used in the form of conventional cosmetic formulations.

Compared with known naturally occurring, soluble collagen, soluble elastin has a decisive advantage. The molecular weight of soluble elastin is considerably less than that of collagen, which is of the order of 300,000 with small amounts of up to about 100,000.

However, it is known that the limit for skin penetration is at a molecular weight of about 20,000 [Bonnisegni CH., Kosmetika 4 (1976), 35-36]. Accordingly, about 90% of the soluble elastin according to the invention is capable of skin penetration, whereby the conditions for effective biological action are optimally fulfilled.

Example 1: (Spray)

| | | |
|---|---|---|
| A | Cetylsteryl alcohol | 3.00% |
| | Fatty alcohol polyglycol ether | 8.00% |
| | Decyl oleate | 10.00% |
| | Triglycerol mixture various natural fats | 20.00% |
| | p-Hydroxybenzoic acid propyl ester | 0.02% |
| B | Water (demineralised) | 56.08% |
| | Na dehydracetate | 0.2% |
| | p-Hydroxylbenzoic acid methyl ester | 0.2% |
| C | soluble Elastin, 0.2–0.5% strength solution, prepared as described above | 2.00% |
| D | Perfume oil | 0.50% |

The components mentioned under part A are mixed and warmed to 70° C. Mixture B is boiled up, cooled to 75° C. and added to part A, whilst stirring. Whilst stirring, the mixture is cooled to 35° C. and, parts C and D are added.

The finished formulation is filled into an aerosol container and propellent gas is added. It can be taken out of the vessel in the form of a foam.

Example 2: Water-in-oil type emulsion (emulsion ointment)

| | | |
|---|---|---|
| A | Mixture of a higher molecular fatty alcohol, wax esters and fats | 20.00% |
| | Decyl oleate | 10.00% |
| | White petroleum jelly | 10.00% |
| | Triglycerol mixture of various natural fats | 10.00% |
| | p-Hydroxybenzoic acid propyl ester | 0.02% |
| B | Water | 44.08% |
| | Dehydracetate | 0.20% |
| | p-Hydroxybenzoic acid methyl ester | 0.20% |
| C | Soluble Elastin, 0.2–0.5% strength solution prepared as described above | 5.00% |
| D | Perfume oil | 0.50% |

The emulsion is prepared by a method similar to that of Example 1.

Example 3: Oil-in-water type emulsion

| | |
|---|---|
| A | Self-emulsifying mixture of monoglycerides and diglycerides of higher, |

-continued

| | | |
|---|---|---|
| | saturated fatty acids | 16.00% |
| | Fatty alcohol polyglycol ether | 1.00% |
| | 2-Octyldodecanol | 6.00% |
| | Isopropyl myristate | 4.00% |
| | p-Hydroxybenzoic acid propyl ester | 0.02% |
| B | Glycerol | 6.00% |
| | Water | 56.08% |
| | Na dehydracetate | 0.02% |
| | p-Hydroxybenzoic acid methyl ester | 0.02% |
| C | Soluble Elastin solution (as described above) | 10.00% |
| D | Perfume oil | 0.05% |

The emulsion is prepared by a method similar to that of Example 1.

Example 4: Face cream

| | | |
|---|---|---|
| A | Sodium cetylstearyl sulphate | 0.8% |
| | Cetylstearyl alcohol | 7.2% |
| | Wool grease | 2.0% |
| | Isopropyl palmitate | 14.5% |
| | 2-Octyl-dodecanol | 10.0% |
| B | Water (demineralised) | 57.5% |
| | Propylene 1,2-glycol | 5.0% |
| C | Soluble Elastin solution (as described above) | 3.0% |
| D | Perfume oil | 9.5% |
| | Preservative | 9.5% |

The face cream is prepared by a method similar to that of Example 1.

Example 5: After-sun lotion

| | | |
|---|---|---|
| A | Decyl oleate | 2.5% |
| | Isopropyl myristate | 2.5% |
| | Liquid paraffin | 4.0% |
| | Polyoxyethylene stearate | 0.9% |
| | Sorbitane monostearate | 0.6% |
| B | Water (demineralised) | 77.4% |
| | Ethyl alcohol | 10.0% |
| | Allantoin | 0.1% |
| C | Soluble Elastin solution (as described above) | 2.0% |
| D | Perfume oil | 9.5% |
| | Preservative | 9.5% |

The after-sun lotion is prepared by a method similar to that of Example 1.

What is claimed is:

1. A cosmetic agent containing as an active ingredient soluble elastin in which about 80% of said soluble elastin has a molecular weight in the range of from 3,000 to 10,000, about 10% of said soluble elastin has a molecular weight of about 10,000 to 25,000 and about 10% of said soluble elastin has a molecular weight in the range of 25,000 to 100,000, in an amount effective to combat skin withering for a visible cosmetic effect (1) in admixture with a solid or liquefied gaseous diluent or (2) in admixture with a liquid diluent.

2. A cosmetic agent according to claim 1 in which the soluble elastin has been obtained by the mild hydrolysis of elastin.

3. A cosmetic agent according to claim 2 in which the hydrolysis is effected by boiling in oxalic acid and any residual oxalic acid is removed after hydrolysis.

4. A cosmetic agent according to claim 1 containing up to 0.05% by weight of the soluble elastin.

5. A cosmetic agent according to claim 4 containing from 0.004 to 0.025% by weight of the soluble elastin.

6. A cosmetic agent according to claim 1 in the form of an emulsion, lotion, spray, ointment, cream or foam mask.

7. A method of combating skin ageing in human and non-human animals which comprises applying to the animals' skin a cosmetic agent according to claim 1.

* * * * *